United States Patent
Livesay et al.

(10) Patent No.: US 10,629,310 B2
(45) Date of Patent: Apr. 21, 2020

(54) SYSTEMS AND METHODS FOR FACILITATING COMMUNICATION OF HEALTH INFORMATION

(71) Applicant: Michigan Health Information Network Shared Services, East Lansing, MI (US)

(72) Inventors: Jeff Livesay, Bloomfield, MI (US); Tim Pletcher, Mount Pleasant, MI (US)

(73) Assignee: Michigan Health Information Network Shared Services, East Lansing, MI (US)

(*) Notice: Subject to any disclaimer, the term of this patent is extended or adjusted under 35 U.S.C. 154(b) by 0 days.

(21) Appl. No.: 15/855,319

(22) Filed: Dec. 27, 2017

(65) Prior Publication Data

US 2019/0198181 A1    Jun. 27, 2019

(51) Int. Cl.
| | |
|---|---|
| *G16H 80/00* | (2018.01) |
| *G16H 10/60* | (2018.01) |
| *G16H 50/20* | (2018.01) |
| *H04L 29/06* | (2006.01) |
| *H04L 29/08* | (2006.01) |
| *G06F 16/951* | (2019.01) |

(52) U.S. Cl.
CPC .......... *G16H 80/00* (2018.01); *G06F 16/951* (2019.01); *G16H 10/60* (2018.01); *G16H 50/20* (2018.01); *H04L 67/12* (2013.01); *H04L 67/2823* (2013.01); *H04L 69/08* (2013.01); *H04L 69/18* (2013.01)

(58) Field of Classification Search
CPC ......... G16H 80/00; G06F 19/30; G06F 19/32; G06F 19/34; G06F 17/30864; G06Q 50/22; G06Q 50/24; H04L 67/12; H04L 41/0226
See application file for complete search history.

(56) References Cited

U.S. PATENT DOCUMENTS

| | | | |
|---|---|---|---|
| 5,155,802 A | 10/1992 | Mueller et al. | |
| 5,804,373 A | 9/1998 | Schweitzer et al. | |
| 6,260,021 B1 * | 7/2001 | Wong ................... | G06F 19/321 707/999.103 |

(Continued)

*Primary Examiner* — Nam T Tran
(74) *Attorney, Agent, or Firm* — Honigman LLP

(57) ABSTRACT

This disclosure provides systems and methods for facilitating communication of health information. A system can include a request management module to receive, from a source endpoint, an electronic query. The query can be formatted according to a first communications protocol and can include at least one request parameter. A destination identifier module can determine a destination endpoint and a second destination endpoint. A translation module can translate the electronic query from the first communications protocol to a second communications protocol associated with the destination endpoint to generate a translated query. The translation module can also translate the electronic query from the first communications protocol to a third communications protocol associated with the second destination endpoint to generate a second translated query. The request management module can transmit the translated query and the second translated query to the destination endpoint and the second destination endpoint, respectively.

16 Claims, 3 Drawing Sheets

(56) References Cited

U.S. PATENT DOCUMENTS

2003/0212673 A1* 11/2003 Kadayam .......... G06F 17/30864
707/999.003
2016/0283666 A1* 9/2016 Kutscher ................. G06F 19/00
2019/0180862 A1* 6/2019 Wisser .................... G06F 16/51

* cited by examiner

SYSTEMS AND METHODS FOR FACILITATING COMMUNICATION OF HEALTH INFORMATION

BACKGROUND

A large volume of medical information can be stored electronically for individuals or populations. For example, information relating to patients' diagnosed conditions, prescribed treatments, health outcomes, medical procedures undergone, and other information can be recorded across a wide variety of computing devices, such as servers maintained by different health organizations. Often, these health organizations may store such information in different formats, and may be configured to communicate according to different communications protocols. As a result of the numerous disparate systems that store such information, and the numerous protocols used for communicating with these disparate systems, requesting and obtaining such information electronically can be challenging.

SUMMARY

One aspect of this disclosure is directed to a system for facilitating communication of health information. The system can include a request management module configured to receive, from a source endpoint, an electronic query corresponding to a request for health information. The query can be formatted according to a first communications protocol and can include at least one request parameter. The system can include a destination identifier module configured to determine a destination endpoint based on the electronic query. The system can include a translation module configured to determine a second communications protocol associated with the destination endpoint. The translation module can also be configured to translate the electronic query from the first communications protocol to the second communications protocol to generate a translated query. The request management module can be further configured to transmit the translated query to the destination endpoint. The system can include a response management module configured to receive, from the destination endpoint, a response to the translated query. The response can be formatted according to the second communications protocol.

In some implementations, the translation module can be further configured to translate the response from the second communications protocol to the first communications protocol to generate a translated response. The response management module can be further configured to transmit the translated response to the destination endpoint. In some implementations, the response management module can be further configured to parse the response received from the destination endpoint to extract at least one response parameter from the response. The at least one response parameter can correspond to the at least one request parameter.

In some implementations, the destination identifier module can be further configured to parse the electronic query according to the first communications protocol to extract information corresponding to an identification of the destination endpoint. In some implementations, the electronic query may not specify the destination endpoint. The destination identifier module can be further configured to determine the destination endpoint based on the at least one request parameter.

In some implementations, the destination identifier module can be further configured to determine at least a second destination endpoint based on the at least one request parameter. In some implementations, the translation module can be further configured to determine a third communications protocol associated with the second destination endpoint, and to translate the electronic query from the first communications protocol to the third communications protocol to generate a second translated query. The request management module can be further configured to transmit the second translated query to the second destination endpoint. In some implementations, the response management module can be further configured to receive, from the second destination endpoint, a second response to the second translated query. The second response can be formatted according to the third communications protocol.

In some implementations, the response management module can be further configured to compile information included in the response and information included in the second response to generate a compiled response. The translation module can be further configured to translate the compiled response into the first communications protocol. The response management module can be further configured to transmit the compiled response to the source endpoint. In some implementations, the translation module can be further configured to generate an intermediate structure based on the electronic query. The intermediate structure can include the at least one request parameter and at least one expected response type.

Another aspect of this disclosure is directed to a method for facilitating communication of health information. The method can include receiving, by a request management module from a source endpoint, an electronic query corresponding to a request for health information. The query can be formatted according to a first communications protocol and can include at least one request parameter. The method can include determining, by a destination identifier module, a destination endpoint based on the electronic query. The method can include determining, by a translation module, a second communications protocol associated with the destination endpoint. The method can include translating, by the translation module, the electronic query from the first communications protocol to the second communications protocol to generate a translated query. The method can include transmitting, by the request management module, the translated query to the destination endpoint. The method can include receiving, by a response management module from the destination endpoint, a response to the translated query. The response can be formatted according to the second communications protocol.

In some implementations, the method can include translating, by the translation module, the response from the second communications protocol to the first communications protocol to generate a translated response. The method also can include transmitting, by the response management module, the translated response to the destination endpoint. In some implementations, the method can include parsing, by the response management module, the response received from the destination endpoint to extract at least one response parameter from the response. The at least one response parameter can correspond to the at least one request parameter.

In some implementations, the method can include parsing, by the destination identifier module, the electronic query according to the first communications protocol to extract information corresponding to an identification of the destination endpoint. In some implementations, the electronic query may not specify the destination endpoint. The method can further include determining, by the destination identifier module, the destination endpoint based on the at least one request parameter.

In some implementations, the method can include determining, by the destination identifier module, at least a second destination endpoint based on the at least one request parameter. In some implementations, the method can include determining, by the translation module, a third communications protocol associated with the second destination endpoint. The method can also include translating, by the translation module, the electronic query from the first communications protocol to the third communications protocol to generate a second translated query. The method can also include transmitting, by the request management module, the second translated query to the second destination endpoint. In some implementations, the method can include receiving, by the response management module from the second destination endpoint, a second response to the second translated query. The second response can be formatted according to the third communications protocol.

In some implementations, the method can include compiling, by the response management module, information included in the response and information included in the second response to generate a compiled response. The method can also include translating, by the translation module, the compiled response into the first communications protocol. The method can also include transmitting, by the response management module, the compiled response to the source endpoint. In some implementations, the method can include generating, by the translation module, an intermediate structure based on the electronic query. The intermediate structure can include the at least one request parameter and at least one expected response type.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing.

DETAILED DESCRIPTION

Figure 1:
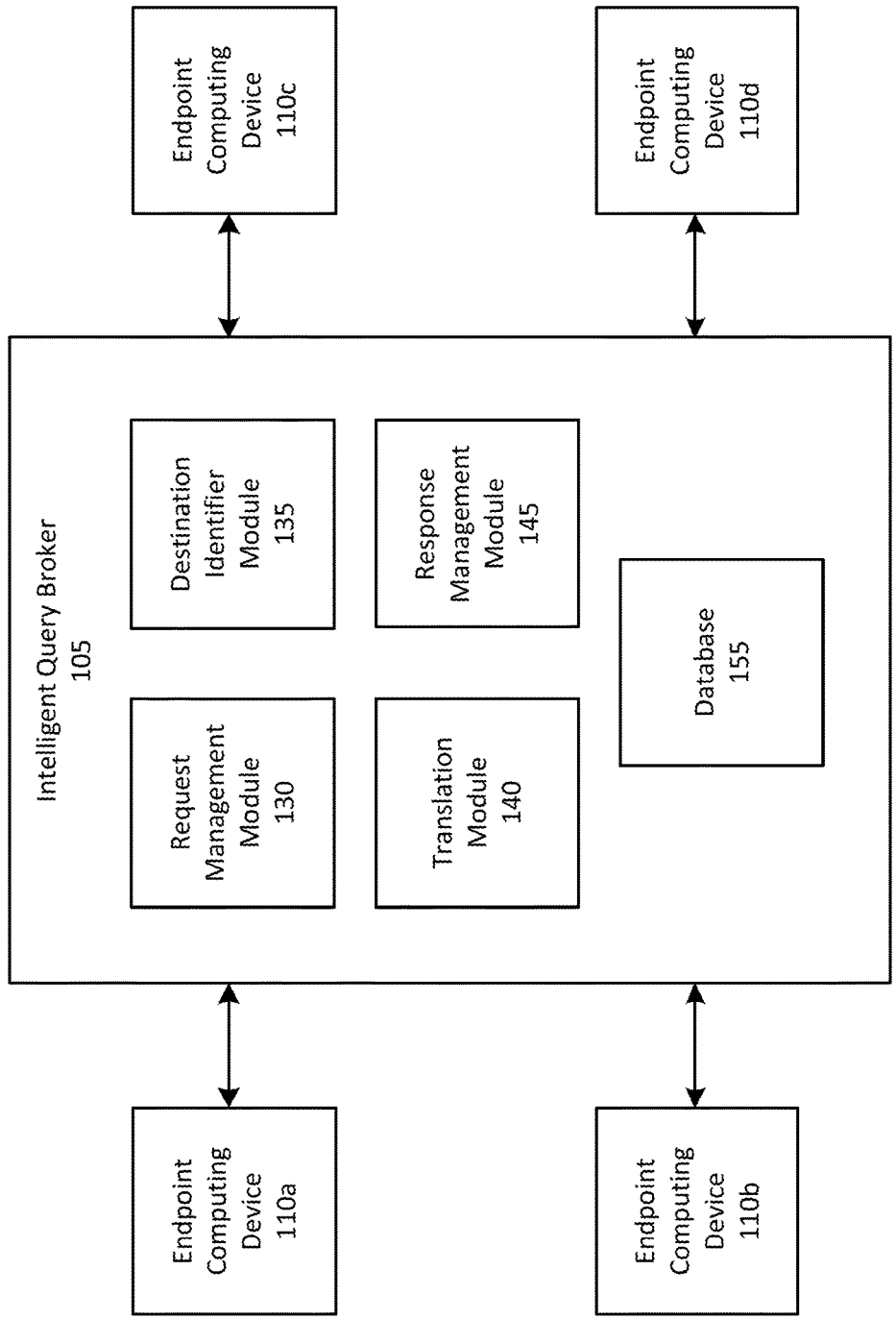
FIG. 1 illustrates an example system for facilitating communication of health information, according to an illustrative implementation.

Following below are more detailed descriptions of various concepts related to, and implementations of systems and methods for facilitating communication of health information. The various concepts introduced above and discussed in greater detail below may be implemented in any of numerous ways, as the described concepts are not limited to any particular manner of implementation. Examples of specific implementations and applications are provided primarily for illustrative purposes.

As described above, in the healthcare field a large volume of health information is stored electronically. New health information can be generated each time a patient experiences a health event resulting in contact with a health organization. For example, each time a patient is admitted to a hospital, visits a physician's office, makes an insurance claim, or obtains medication from a pharmacy, new health information can be generated and stored to keep a record of the event. In some instances, such information may become part of the patient's electronic health record (EHR).

The information generated in this manner can be stored across a wide range of health systems. For example, information corresponding to a patient's hospital visit may be stored by a health information system maintained by the hospital. Similarly, information corresponding to the patient's insurance claim may be stored by a health information system maintained by the health insurance company that processes the claim, and information corresponding to the patient's prescribed medication may be stored by a health information system maintained by the pharmacy that fills the prescription. Thus, the medical information for a single patient may be distributed across a wide range of health information systems. In general, any health organization, such as a hospital, a health plan, a medical insurer, a prescription benefit manager, a pharmacy, or a clinic, may maintain one or more health information systems each storing health information for any number of patients.

Often, the separate health information systems described above may not exchange information with one another on a regular basis. For example, while information for a given patient may be stored by both a hospital health information system and a medical insurer, neither the hospital nor the medical insurer may have a complete set of health information for the patient, because each may not have access to the information stored by the other. As a result, obtaining health information for a single patient can be difficult because it may not be clear where the desired information is stored. This problem becomes more complex when trying to obtain health information for a population of multiple patients, all of whom may have health data stored by disparate health systems.

In addition, the health information systems described above may not even be capable of exchanging health information with one another, due to differences in their particular implementations. For example, a first health information system may be configured to communicate according to a first communications protocol that may be incompatible with a second communications protocol used by a second health information system. Additionally, the two health information systems may be configured to respond to queries that are structured differently. Thus, it may be difficult or impossible for two such health information systems to exchange health information. In this scenario, it can also be difficult for a third party to obtain health information from both health information systems, because the third party must be capable of communicating according to both the first communications protocol and the second communications protocol, and must have knowledge of the query structures expected by each of the health information systems, in order to successfully request and receive information from both health information systems.

This disclosure provides systems and methods for facilitating communication of health information through the use of an intelligent query broker. The intelligent query broker serves as a technical solution to the technical challenges described above. For example, the intelligent query broker can be configured to receive a query for health information from a source endpoint, and to determine one or more destination endpoints corresponding to health information systems that may store the information requested by the query. The intelligent query broker can also adaptively translate the query into various formats associated with the respective destination endpoints, forward the translated queries to the destination endpoints, and receive responses to the queries from the destination endpoints. The intelligent query broker can then return any information received in the responses back to the source endpoint. The intelligent query broker therefore helps to resolve the challenges that result from the distributed storage of health information across a wide range of health information systems that may be incompatible with one another. These and other aspects of this disclosure are described further below.

FIG. 1 illustrates an example system 100 for facilitating communication of health information, according to an illustrative implementation. The system 100 includes an intelligent query broker 105 and a plurality of endpoint computing devices 110a-110d (generally referred to as endpoint computing devices 110). The intelligent query broker 105 includes a request management module 130, a destination identifier module 135, a translation module 140, a response management module 145, and a database 155.

The intelligent query broker 105 is configured to facilitate communication of health information between the endpoint computing devices 110. For example, the endpoint computing devices 110 can each correspond to a respective entity involved in the management and storage of health information. In some implementations, the each endpoint computing device 110 can be a computing device associated with a patient, a healthcare provider (e.g., a physician or a pharmacist), or a health organization. It should be understood that, while four endpoint computing devices 110 are depicted in FIG. 1 for illustrative purposes, in practice the system 100 may include any number of endpoint computing devices 110.

In some implementations, one or more of the endpoint computing devices 110 may each include or may be coupled to a health information system storing health and medical data for one or more patients or populations. Generally, the endpoint computing devices 110 may each act as a server or virtualized service configured to initiate and/or respond to queries for health information. Thus, each endpoint computing device 110 may be uniquely identified by a respective email address, uniform resource locator (URL), or any other type or form of unique electronic address. In some implementations, each endpoint computing device 110 may be implemented as any type or form of computing device, including desktop computers, laptop computers, tablet computers, servers, mobile computing devices, handheld computing devices, and the like. It should be understood that each endpoint computing device 110 may be configured to communicate according to a respective communications protocol that may not be compatible with other endpoint computing devices 110, and that each endpoint computing device 110 may be configured to generate and respond to electronic queries for health information in a respective query structure that may not be the same as the query structures used by other endpoint computing devices 110.

The intelligent query broker 105 can receive electronic queries from an endpoint computing device 110, determine at least one second endpoint computing device 110 to receive the query, and perform any required processing of the electronic query to ensure that the second endpoint computing device 110 is capable of receiving and responding to the electronic query. As described above, an electronic query may include any type or form of request for health information. Generally, a query may include one or more request parameters that specify the information requested by the query. For example, a request parameter may correspond to an entity (such as a healthcare provider, a patient, or a population of patients) for whom health information is requested. A request parameter also may specify a quality measure, a characteristic, or a value identifying the type of information requested. For example, a request parameter may indicate a health condition to which the query pertains.

A query may relate to a request for any type of health information, and may include any number of parameters. In one example, a query may correspond to a request for a list of patients residing in a town who have been diagnosed with diabetes. Such a query may include a request parameter specifying the town (e.g., a zip code), a request parameter specifying the health condition in question (i.e., diabetes), and a request parameter specifying the type of information requested (i.e., a list of all patients meeting the conditions specified by the first two request parameters). In another example, a query may correspond to a request for a list of medications that have been prescribed to a particular patient in the last five years. Such a request may include a request parameter specifying the patient (e.g., the patient's name, social security number, or other identifying information), a request parameter specifying the time period in question (i.e., the previous five years), and a request parameter specifying the type of information requested (i.e., a list of the patient's prescribed medications). It should be understood that the techniques described in this disclosure can be applied to any type of query including any number of request parameters. The particular types of queries used in the examples described herein are illustrative only, and should not be construed as limiting the scope of this disclosure.

The request management module 130 can be configured to receive a query from any of the endpoint computing devices 110. A endpoint computing device 110 from which a query is received by the request management module 130 can be referred to as a source endpoint computing device 110. The received query can be formatted according to a first communications protocol associated with the source endpoint computing device 110. For example, the query may be formatted according to protocols such as Health Level 7 (HL7), Query By Parameter (QBP) as promoted by the Center for Disease Control, Fast Healthcare Interoperability Resources (FHIR), the Integrating the Healthcare Enterprise (IRE) framework, Cross Community Discovery (XDS), or any other suitable communications protocol.

The request management module 130, the destination identifier module 135, and the translation module 140 together can facilitate routing of the query to an appropriate one of the endpoint computing devices 110 referred to as a destination endpoint computing device 110. The destination identifier module 135 can be configured to determine the destination endpoint computing device 110. In some implementations, an address (e.g., an email address or URL) of the destination endpoint computing device 110 can be included in the electronic query itself, and the destination identifier module 135 can be configured to extract information corresponding to the address of the intended destination endpoint computing device 110. For example, the query may include a request parameter that specifies the destination endpoint computing device 110. The destination identifier module 135 can parse the query in a manner consistent with the communications protocol in which the query was received to extract the request parameter that corresponds to the destination endpoint computing device 110. In another example, the query may not specify any intended destination, and the destination identifier module 135 can be configured to determine the destination endpoint computing device 110 based on other request parameters included in the query. For example, if the query includes one or more request parameters corresponding to the population of a particular state, the destination identifier module 135 can determine that the query should be transmitted to a destination endpoint computing device 110 that is operated by a health organization located in that state.

In some implementations, the destination identifier module 135 can also identify more than one destination endpoint computing device 110 that should receive the query. For example, as described above, health information for a given patient may reside across multiple health information systems each corresponding to a respective endpoint computing device 110. Thus, for a query that requests health information for a particular patient, the destination identifier module 135 can be configured to identify two or more destination endpoint computing devices 110 that may be likely to maintain health information for the patient.

After a destination endpoint computing device 110 has been identified, the translation module 140 can be configured to determine a second communications protocol associated with the identified destination endpoint computing device 110. For example, the translation module 140 can maintain a list of the communications protocols that are compatible with each of the endpoint computing devices 110, and can identify the second communications protocol by referring to the list. In some implementations, such a list can be stored in the database 155, and the translation module 140 can retrieve the list from the database 155.

As described above, while many such communications protocols exist, each endpoint computing device 110 may support only a subset of these protocols. In some implementations, one or more of the endpoint computing devices 110 may each support only a single communications protocol, and may be unable to process queries using different protocols. As a result, simply forwarding the query to a destination endpoint computing device 110 for processing may not be effective, depending on the communications protocols and query formats supported by the source endpoint computing device 110 and the destination endpoint computing device 110.

If the second communications protocol identified by the translation module 140 is different from the first communications protocol of the source endpoint computing device 110, the translation module 140 can also be configured to translate the query from the first communications protocol to the second communications protocol. In some implementations, the translation module 140 can maintain a set of rules for translating a query from one communications protocol to another, and can process the query according to these rules to generate a translated query that is formatted according to the second communications protocol. In implementations in which the destination identifier module 135 identifies more than one destination endpoint computing device 110, the translation module 140 can be configured to generate a unique translated query for each destination endpoint computing device 110 whose communication protocol differs from the communications protocol according to which the query is formatted.

After the translation module 140 has generated the translated query, the request management module 130 can transmit the translated query to the identified destination endpoint computing device 110. If multiple destination endpoint computing devices 110 were identified and multiple translated queries were generated for the respective destination endpoint computing devices 110, the request management module 130 can forward each translated query to its respective destination endpoint computing device 110. Thus, each destination endpoint computing device 110 can receive a translated query that is formatted in a communications protocol consistent with the destination endpoint computing device 110, regardless of the communications protocol supported by the source endpoint computing device 110.

As will be discussed further below, in some implementations, the translation module 140 can also perform steps to help with the processing of an eventual response from a destination endpoint computing device 110. For example, because responses may be received in a variety of formats (e.g., according to the different communications protocols that may be used by different destination endpoint computing devices 110), the translation module 140 can be configured to generate an intermediate structure that can be referenced in order to interpret a response. The intermediate structure can include any or all of the request parameters of the electronic query, in addition to an expected response type. The expected response type can be determined based on the information in the query. For example, the expected response type may be a number, a percentage, an identification of one or more patients, an identification of a health organization such as a hospital or a medical insurer, a Boolean response (e.g., true or false, or yes or no), etc. In some implementations, the response type also can include information corresponding to the communications format expected for the response to the query. The translation module 140 can generate the intermediate structure in any suitable form, including any type of data structure, document, or file type. In some implementations, the translation module 140 can generate the intermediate structure as an XML document or other table having a first portion for storing the request parameters of the query and a second portion for storing the expected response type.

The response management module 145 can be configured to receive a response to the query from a destination endpoint computing device 110. Generally, the response may be formatted according to the communications protocol expected by the destination endpoint computing device 110 (e.g., the protocol into which the translation module 140 translates the query before the request management module 130 transmits the query to the destination endpoint computing device 110). The response can include at least one response parameter that provides the information requested by the query. Thus, the response parameter can correspond to at least one of the request parameters of the original query.

In some implementations, the response management module 145 can be configured to parse the response received from the destination endpoint computing device 110 to extract the response parameter. As described above, the response may be formatted in a variety of ways depending on the communications protocol used by the destination endpoint computing device 110. To facilitate the process of parsing the response to extract the response parameter, the response management module 145 may refer to information included in the intermediate structure generated by the translation module 140 described above. For example, the response management module 145 may examine the intermediate structure in order to determine the expected response type, and may then parse the response to extract information corresponding to the response type, which the response management module 145 can identify as the response parameter. It should be understood that, in some implementations, a response may include more than one response parameter, and the response management module 145 can be configured to extract any response parameters that are relevant to the information requested by the original query.

In implementations in which multiple translated queries were transmitted to multiple destination endpoint computing devices 110 by the request management module 130, the response management module 145 can receive multiple responses. The response management module 145 can process each response in the manner described above to extract the relevant response parameters from each response. In some implementations, the response management module 145 can combine information included in multiple responses together. For example, the response management module 145 can be configured to compile the extracted response parameters from two or more responses into a single unit that can be referred to as a compiled response. In some implementations, the compiled response may aggregate the response parameters from multiple responses. In one example, if the original query requested a number of patients in a given population who are diagnosed with a specified medical condition and the query was provided to two destination endpoint computing devices 110, the response management module 145 can extract the numbers received in both responses (i.e., the response parameters for both responses) and sum them together to generate the compiled response. In another example, the original query may request an identity of each patient in a given population who has been diagnosed with a specified medical condition. Thus, each response will include a list of such patients. In this scenario, the response management module 145 can be configured to concatenate the list of patients identified in each response to produce a single compiled list. In some implementations, the response management module 145 also can be configured to eliminate repeated entries from the compiled list, for example if both responses identified two or more of the same patients.

After the response management module 145 has extracted the response parameter from a response (and generated a compiled response if more than one response was received), the translation module 140 can be configured to translate the response (or the compiled response) into the communications protocol associated with the original source endpoint computing device 110, in a manner similar to that described above for translation of the original query. The response management module 145 can then transmit the response (or the compiled response) back to the source endpoint computing device 110. Thus, the source endpoint computing device 110 can transmit a single query to the intelligent query broker 105, and the modules of the intelligent query broker 105 can translate the query, provide the query to one or more destination endpoint computing devices 110 in the appropriate communications protocols, compile any responses received from the destination endpoint computing devices 110, and provide the compiled response back to the source endpoint computing device 110. As a result, the source endpoint computing device 110 does not have to be capable of communicating according to the communications protocols used by any of the destination endpoint computing devices 110, yet still can request and receive information stored by them.

Figure 2:
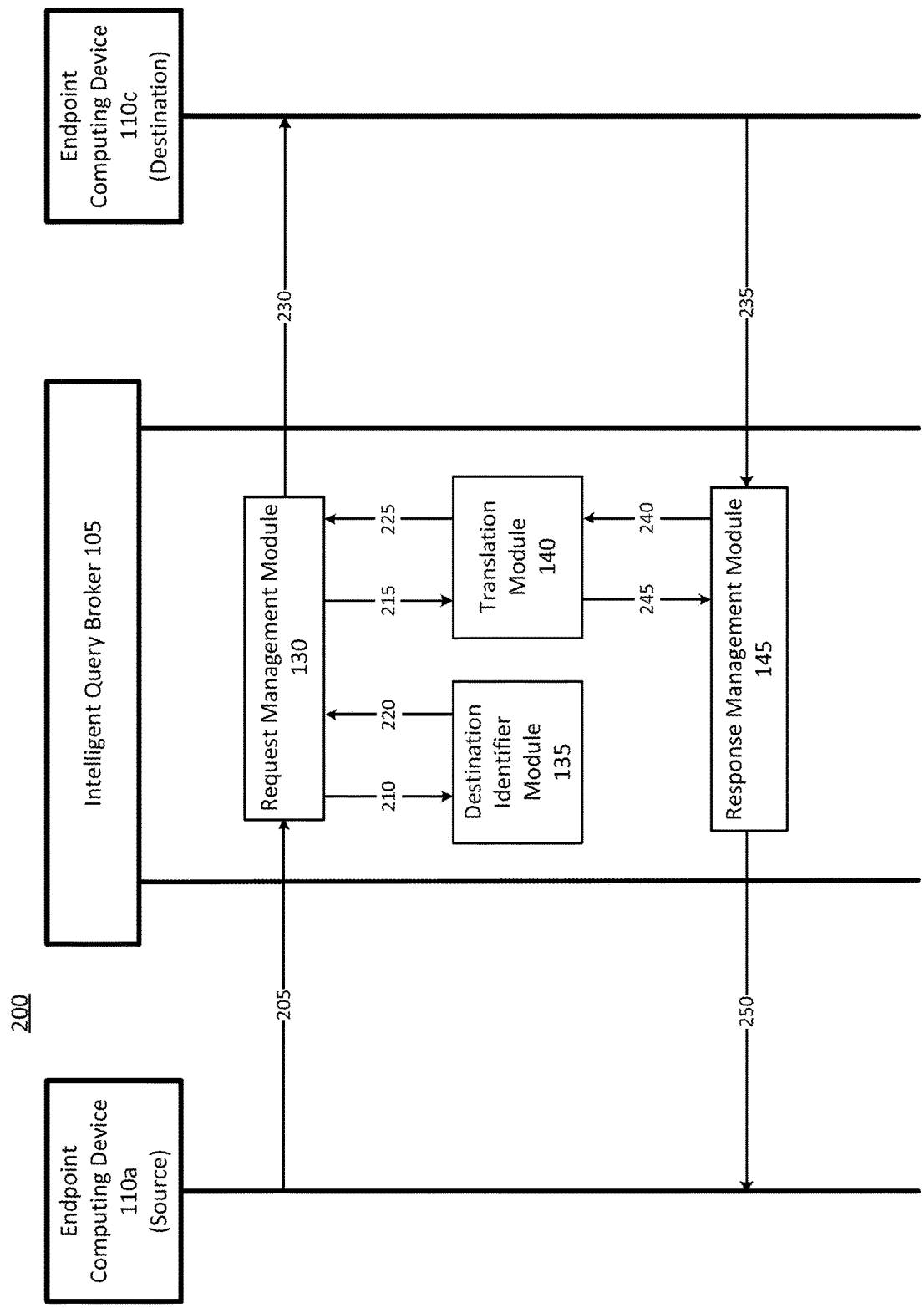
FIG. 2 illustrates a sequence diagram showing the flow of information within the system of FIG. 1, according to an illustrative implementation.

FIG. 2 illustrates a sequence diagram 200 showing the flow of information within the system 100 of FIG. 1, according to an illustrative implementation. Referring now to FIG. 2, and with reference also to FIG. 1, the sequence diagram 200 shows the flow of information between the endpoint computing device 110a (which acts as a source endpoint computing device 110), the intelligent query broker 105, and the endpoint computing device 110c (which acts as a destination endpoint computing device 110). It should be understood that the selection of the endpoint computing device 110a and the endpoint computing device 110c as source and destination, respectively, is made only for illustrative purposes and that, in other examples, any of the endpoint computing devices 110 could serve as either the source or destination. Generally, in the sequence diagram 200, arrows represent information transmitted between these components.

At step 205, the endpoint computing device 110a transmits a query to the intelligent query broker 105, which is received by the request management module 130. At step 210, the request management module 130 provides the query to the destination identifier module 135 to allow the destination identifier module 135 to process the query to determine one or more destinations for the query as described above. At step 215, the request management module 130 provides the query to the translation module 140 to enable the translation module 140 to translate the query into the communications format expected by the destination endpoint computing device 110c.

At step 220, the destination identifier module 135 provides the destination address to the request management module 130, and at step 225, the translation module 140 provides the translated query to the request management module 130. The request management module 130 then forwards the translated query to the destination endpoint computing device 110c at step 230.

At step 235, the destination endpoint computing device 110c provides a response to the query back to the intelligent query broker 105, and the response is received by the response management module 145. The response management module 145 extracts any relevant response parameters from the response and provides them to the translation module 140, which generates a translated response. The translated response is provided from the translation module 140 to the response management module 145 at step 245. At step 250, the response management module 145 provides the translated response to the source endpoint computing device 110a.

As can be seen in the figure, the communications sent by the source endpoint computing device 110a and the destination endpoint computing device 110c are relatively simple, including only a query and a response. A majority of the manipulation of the query and response to allow the source endpoint computing device 110a and the destination endpoint computing device 110c to communicate with one another is performed within the intelligent query broker 105. Furthermore, the details of the processing performed by the intelligent query broker 105 are abstracted from both the source endpoint computing device 110a and the destination endpoint computing device 110c. Thus, communications between the source endpoint computing device 110a and the destination endpoint computing device 110c can be carried out in a simplified manner through the use of the intelligent query broker 105.

Figure 3:
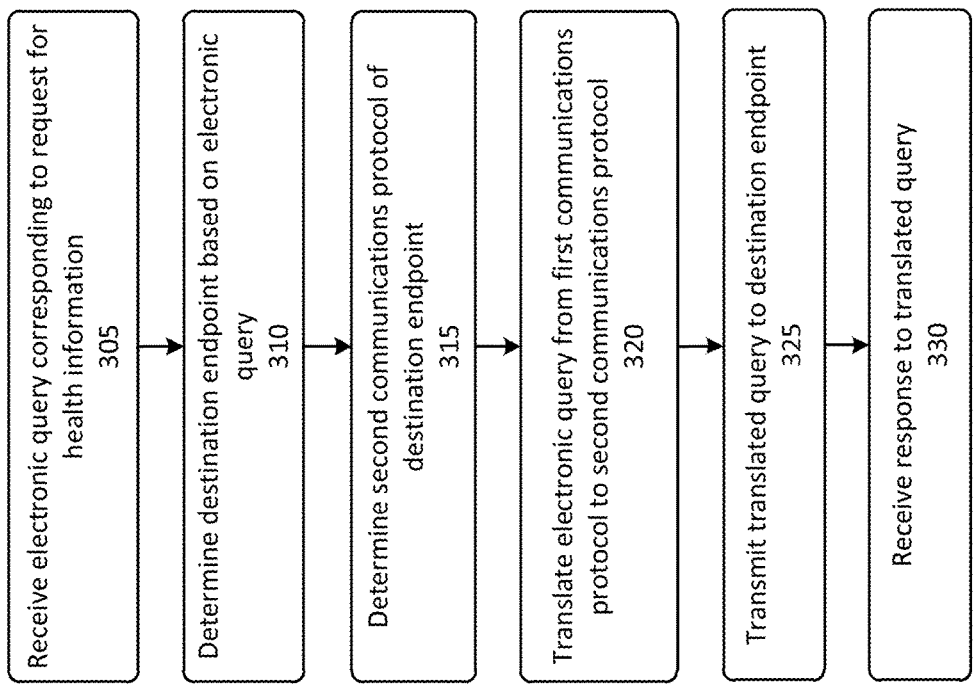
FIG. 3 illustrates a flowchart of an example method for facilitating communication of health information, according to an illustrative implementation.

FIG. 3 illustrates a flowchart of an example method 300 for facilitating communication of health information, according to an illustrative implementation. In some implementations, the method 300 can be performed by the intelligent query broker 105 shown in FIG. 1. In brief overview, the method 300 includes receiving an electronic query corresponding to a request for health information (operation 305), determining a destination endpoint based on the electronic query (operation 310), determining a second communications protocol of the destination endpoint (operation 315), translating the electronic query from a first communications protocol to the second communications protocol (operation 320), transmitting the translated query to the destination endpoint (operation 325), and receiving a response to the translated query (operation 330).

Referring again to FIG. 3, the method 300 includes receiving an electronic query corresponding to a request for health information (operation 305). This operation can be performed, for example, by the request management module 130 shown in FIG. 1. In some implementations, the request can be received from a source endpoint, which may correspond to any of the endpoint computing devices 110 shown in FIG. 1. The received query can be formatted according to a first communications protocol associated with the source endpoint. For example, the query may be formatted according to protocols such as HL7, QBP, FHIR, IHE, XDS, or any other suitable communications protocol.

The method 300 includes determining a destination endpoint based on the electronic query (operation 310). In some implementations, this operation can be performed by the destination identifier module 135 shown in FIG. 1. In some implementations, the destination endpoint can correspond to one of the endpoint computing devices 110 shown in FIG. 1. In some implementations, an address of the destination endpoint computing device 110 can be included in the electronic query, and the destination identifier module 135 can be configured to extract information corresponding to the address of the intended destination endpoint computing device 110. In some other implementations, the query may not specify any intended destination, and the destination identifier module 135 can be configured to determine the destination endpoint computing device 110 based on other request parameters included in the query. In some implementations, the destination identifier module 135 can also identify more than one destination endpoint computing device 110 that should receive the query.

The method 300 includes determining a second communications protocol of the destination endpoint (operation 315). In some implementations, this operation can be performed by the translation module 140 shown in FIG. 1. For example, the translation module 140 can maintain a list of the communications protocols that are compatible with each of the endpoint computing devices 110, and can identify the second communications protocol by referring to the list. In operation 320, the translation module 140 can translate the electronic query from the first communications protocol to the second communications protocol. In some implementations, the translation module 140 can maintain an application programming interface (API) or a different set of rules or instructions that maps the components of one communications protocol to those of another. The translation module 140 can refer to these rules or instructions to generate a translated query that is formatted according to the second communications protocol.

The method 300 includes transmitting the translated query to the destination endpoint (operation 325). In some implementations, this operation can be performed by the request management module 130. At operation 330, the method 300 includes receiving a response to the translated query (operation 330). In some implementations, this operation can be performed by the response management module 145. The response can be formatted according to the second communications protocol associated with the destination endpoint. The response can include at least one response parameter that provides the information requested by the query. In some implementations, the response management module 145 can extract the at least one response parameter from the response. The translation module 140 can generate a translated response that includes the extracted response parameter formatted according to the first communications protocol, and the response management module 145 can provide the translated response back to the source endpoint.

The embodiments herein may be suitably implemented on conventional computing devices, for example, computer workstations, on Internet-based applications, on optical computing devices, neural computers, biological computers, molecular computing devices, and other devices. As may be appreciated by those skilled in the art, the present invention, in short, may be implemented on any system, automaton, and/or Turing machine.

An automaton is herein described as a mechanism that is relatively self-operating and designed to follow a predetermined sequence of operations or respond to encoded instructions. A Turing machine is herein described as an abstract expression of a computing device that may be realized or implemented on an infinite number of different physical computing devices. Examples of systems, automatons and/or Turing machines that may be utilized in performing the process of the present invention include, but are not limited to: electrical computers (for example, an International Business Machines (IBM) personal computer); neuro-computers (for example, one similar to the "General Purpose Neural Computer" described in U.S. Pat. No. 5,155,802, issued to Paul H. Mueller, on Oct. 13, 1992); molecular computers (for example, one similar to the "Molecular Automata Utilizing Single or Double-Strand Oligonucleotides" described in U.S. Pat. No. 5,804,373, issued to Allan Lee Schweiter et al., on Sep. 8, 1998); biological computers (for example, one similar to the biological computer presented by Ehud Shapiro, of the Computer Science and Applied Mathematics Department at the Weizman Institute of Science (Rehovot, Israel), at the Fifth International Meeting on DNA-Based Computers); and optical computers. For purposes of simplicity, such devices hereinafter are referred to as computers, as is commonly understood in the art. But, the embodiments disclosed herein are not limited being applied to such devices and may be accomplished upon any system or collection of systems capable of providing the features and functions identified herein. For example, the embodiments disclosed herein may be applied to devices such as neuro-synaptic computers, application specific computers (or application specific integrated circuits, sometimes referred to as ASICs), software-defined hardware, domain-specific systems on a chip, processors devoted specifically to artificial intelligence-related tasks, or any computer, processor or chip with a special architecture.

It should be understood that the systems described above may provide multiple ones of any or each of those components and these components may be provided on either a standalone machine or, in some embodiments, on multiple machines in a distributed system. The systems and methods described above may be implemented as a method, apparatus or article of manufacture using programming and/or engineering techniques to produce software, firmware, hardware, or any combination thereof. In addition, the systems and methods described above may be provided as one or more computer-readable programs embodied on or in one or more articles of manufacture. The term "article of manufacture" as used herein is intended to encompass code or logic accessible from and embedded in one or more computer-readable devices, firmware, programmable logic, memory devices (e.g., EEPROMs, ROMs, PROMs, RAMs, SRAMs, etc.), hardware (e.g., integrated circuit chip, Field Programmable Gate Array (FPGA), Application Specific Integrated Circuit (ASIC), etc.), electronic devices, a computer readable non-volatile storage unit (e.g., CD-ROM, floppy disk, hard disk drive, etc.). The article of manufacture may be accessible from a file server providing access to the computer-readable programs via a network transmission line, wireless transmission media, signals propagating through space, radio waves, infrared signals, etc. The article of manufacture may be a flash memory card or a magnetic tape. The article of manufacture includes hardware logic as well as software or programmable code embedded in a computer readable medium that is executed by a processor. In general, the computer-readable programs may be implemented in any programming language, such as LISP, PERL, C, C++, C#, PROLOG, or in any byte code language such as JAVA. The software programs may be stored on or in one or more articles of manufacture as object code.

While various embodiments of the methods and systems have been described, these embodiments are exemplary and in no way limit the scope of the described methods or systems. Those having skill in the relevant art can effect changes to form and details of the described methods and systems without departing from the broadest scope of the described methods and systems. Thus, the scope of the methods and systems described herein should not be limited by any of the exemplary embodiments and should be defined in accordance with the accompanying claims and their equivalents.

What is claimed is:

1. A system for facilitating communication of health information, the system comprising a processor coupled to a memory storing instructions which, when executed by the processor, cause the processor to perform operations comprising:
    receiving, from a source endpoint, an electronic query corresponding to a request for health information of a patient, wherein the electronic query is formatted according to a first communications protocol, includes at least two request parameters, and does not specify a destination endpoint, wherein the at least two request parameters comprise a first request parameter requesting medications prescribed to the patient and a second request parameter specifying a time period associated with the first request parameter, the time period defining a range of times extending from a start time to an end time;
    determining a first destination endpoint and a second destination endpoint different from the first destination endpoint, based on the electronic query;
    determining a second communications protocol associated with the first destination endpoint;
    translating the electronic query from the first communications protocol to the second communications protocol to generate a first translated query associated with the second communications protocol;
    generating an intermediate structure based on the first translated query, the intermediate structure comprising at least one expected response type associated with the at least two request parameters;
    transmitting the first translated query to the first destination endpoint;
    receiving, from the first destination endpoint, a first query response to the first translated query, the first query response formatted according to the second communications protocol and comprising a response parameter providing a list of medications prescribed to the patient from the start time of the time period until the end time of the time period; and
    parsing, using the intermediate structure, the first query response received from the first destination endpoint to extract the response parameter from the first query response, the extracted response parameter corresponding to the at least one expected response type of the intermediate structure.

2. The system of claim 1, wherein the operations further comprise:
    translating the first query response from the second communications protocol to the first communications protocol to generate a first translated response; and
    transmitting the first translated response to the source endpoint.

3. The system of claim 1, wherein the operations further comprise:
    determining a third communications protocol associated with the second destination endpoint;
    translating the electronic query from the first communications protocol to the third communications protocol to generate a second translated query associated with the second communications protocol; and
    transmitting the second translated query to the second destination endpoint.

4. The system of claim 3, wherein the operations further comprise receiving, from the second destination endpoint, a second query response to the second translated query, the second query response formatted according to the third communications protocol.

5. The system of claim 4, wherein the operations further comprise:
    compiling information included in the first query response and information included in the second query response to generate a compiled response;
    translating the compiled response into the first communications protocol; and
    transmitting the compiled response to the source endpoint.

6. The system of claim 1, wherein the intermediate structure further comprises the first request parameter.

7. The system of claim 1, wherein the first communications protocol is one of Health Level 7 (HL7), Query By Parameter (QBP), Fast Healthcare Interoperability Resources (FHIR), Integrating the Healthcare Enterprise (IHE) framework, or Cross Community Discovery (XDS).

8. The system of claim 1, wherein the second communications protocol is one of Health Level 7 (HL7), Query By Parameter (QBP), Fast Healthcare Interoperability Resources (FHIR), Integrating the Healthcare Enterprise (IRE) framework, or Integrating the Healthcare Enterprise (XDS).

9. A method for facilitating communication of health information, the method comprising:
    receiving, by a request management module executing on a processor, from a source endpoint, an electronic query corresponding to a request for health information of a patient, wherein the electronic query is formatted according to a first communications protocol, includes at least two request parameters, and does not specify a destination endpoint, wherein the at least two request parameters comprise a first request parameter requesting medications prescribed to the patient and a second request parameter specifying a time period associated with the first request parameter, the time period defining a range of times extending from a start time to an end time;
    determining, by a destination identifier module executing on the processor, a first destination endpoint and a second destination endpoint different from the first destination endpoint, based on the electronic query;

determining, by a translation module executing on the processor, a second communication protocol associated with the first destination endpoint;

translating, by the translation module, the electronic query from the first communications protocol to the second communications protocol to generate a first translated query associated with the second communications protocol;

generating, by the request management module executing on the processor, an intermediate structure based on the first translated query, the intermediate structure comprising at least one expected response type associated with the at least two request parameters;

transmitting, by the request management module executing on the processor, the first translated query to the first destination endpoint;

receiving, by a response management module executing on the processor, from the first destination endpoint, a first query response to the first translated query, the first query response formatted according to the second communications protocol and comprising a response parameter providing a list of medications prescribed to the patient from the start time of the time period until the end time of the time period; and parsing, by the response management module executing on the processor, using the intermediate structure, the first query response received from the first destination endpoint to extract the response parameter from the first query response, the extracted response parameter corresponding to the at least one expected response type of the intermediate structure.

10. The method of claim 9, further comprising:

translating, by the translation module executing on the processor, the first query response from the second communications protocol to the first communications protocol to generate a first translated response; and transmitting, by the response management module executing on the processor, the first translated response to the source endpoint.

11. The method of claim 9, further comprising:

determining, by the translation module executing on the processor, a third communications protocol associated with the second destination endpoint;

translating, by the translation module executing on the processor, the electronic query from the first communications protocol to the third communications protocol to generate a second translated query associated with the second communications protocol; and transmitting, by the request management module executing on the processor, the second translated query to the second destination endpoint.

12. The method of claim 11, further comprising receiving, by the response management module executing on the processor, from the second destination endpoint, a second query response to the second translated query, the second query response formatted according to the third communications protocol.

13. The method of claim 12, further comprising:

compiling, by the response management module executing on the processor, information included in the first query response and information included in the second query response to generate a compiled response;

translating, by the translation module executing on the processor, the compiled response into the first communication protocol; and transmitting, by the response management module executing on the processor, the compiled response to the source endpoint.

14. The method of claim 9, wherein the intermediate structure further comprises the first request parameter.

15. The method of claim 9, wherein the first communications protocol is one of Health Level 7 (HL7), Query By Parameter (QBP), Fast Healthcare Interoperability Resources (FHIR), Integrating the Healthcare Enterprise (IHE) framework, or Cross Community Discovery (XDS).

16. The method of claim 9, wherein the second communications protocol is one of Health Level 7 (HL7), Query By Parameter (QBP), Fast Healthcare Interoperability Resources (FHIR), Integrating the Healthcare Enterprise (IRE) framework, or Integrating the Healthcare Enterprise (XDS).

* * * * *